(12) United States Patent
Aurilia et al.

(10) Patent No.: US 11,510,554 B1
(45) Date of Patent: Nov. 29, 2022

(54) PLUG FOR ENDOSCOPE ATTACHMENT TIP

(71) Applicant: Motus GI Medical Technologies Ltd., Tirat HaCarmel (IL)

(72) Inventors: Brad D. Aurilia, Coral Springs, FL (US); Brad William Caldeira, Boca Raton, FL (US); Mark Pomeranz, Bernardsville, NJ (US); Andy Scherer, Trabuco Canyon, CA (US); Jeffrey Smith, Irvine, CA (US)

(73) Assignee: Motus GI Methical Technologies Ltd., Tirat HaCarmel (IL)

( * ) Notice: Subject to any disclaimer, the term of this patent is extended or adjusted under 35 U.S.C. 154(b) by 90 days.

(21) Appl. No.: 16/924,341

(22) Filed: Jul. 9, 2020

Related U.S. Application Data

(60) Provisional application No. 62/881,392, filed on Aug. 1, 2019.

(51) Int. Cl.
*A61B 1/00* (2006.01)

(52) U.S. Cl.
CPC ........ *A61B 1/00135* (2013.01); *A61B 1/0008* (2013.01); *A61B 1/0011* (2013.01); *A61B 1/00137* (2013.01); *A61B 1/00142* (2013.01)

(58) Field of Classification Search
CPC ............ A61B 1/00064; A61B 1/00071; A61B 1/0011; A61B 1/00135; A61B 1/0014; A61B 1/00142; A61B 1/00137; A61B 1/00089; A61B 1/0008; A61B 1/00131
See application file for complete search history.

(56) References Cited

U.S. PATENT DOCUMENTS

| | | | | |
|---|---|---|---|---|
| 5,359,991 | A * | 11/1994 | Takahashi | A61B 1/00142 600/122 |
| 5,554,098 | A * | 9/1996 | Yabe | A61B 1/018 600/122 |
| 9,119,532 | B2 * | 9/2015 | Terliuc | A61B 1/00082 |
| 10,264,951 | B2 * | 4/2019 | Terliuc | A61B 1/00082 |
| 2003/0216615 | A1 * | 11/2003 | Ouchi | A61B 1/005 600/144 |
| 2005/0256373 | A1 * | 11/2005 | Bar-Or | A61B 1/00151 600/114 |
| 2007/0179432 | A1 * | 8/2007 | Bar Or | A61B 1/00068 604/30 |
| 2007/0249902 | A1 * | 10/2007 | Aizenfeld | A61B 1/00144 600/124 |
| 2011/0105840 | A1 * | 5/2011 | Terliuc | A61B 1/00131 600/104 |
| 2012/0316391 | A1 * | 12/2012 | Weitzner | A61B 1/00142 600/104 |
| 2016/0022120 | A1 * | 1/2016 | Terliuc | A61B 1/00131 600/124 |
| 2016/0324412 | A1 * | 11/2016 | Hassidov | A61B 1/31 |
| 2019/0231174 | A1 * | 8/2019 | Terliuc | A61B 1/00131 |
| 2020/0260937 | A1 * | 8/2020 | Zhou | A61B 1/042 |

FOREIGN PATENT DOCUMENTS

WO  WO 2015/193896  12/2015

* cited by examiner

*Primary Examiner* — Ryan N Henderson

(57) ABSTRACT

Reversibly attachable pressure-resistant cap for an endoscope sleeve, configured to seal a distal tip of the endoscope sleeve during pressurized inflation of the sleeve to assist insertion of the endoscope into the sleeve. The cap is operable to latch onto the distal tip. The cap is also configured to be easily removed from the distal tip after inflation is no longer needed.

15 Claims, 11 Drawing Sheets

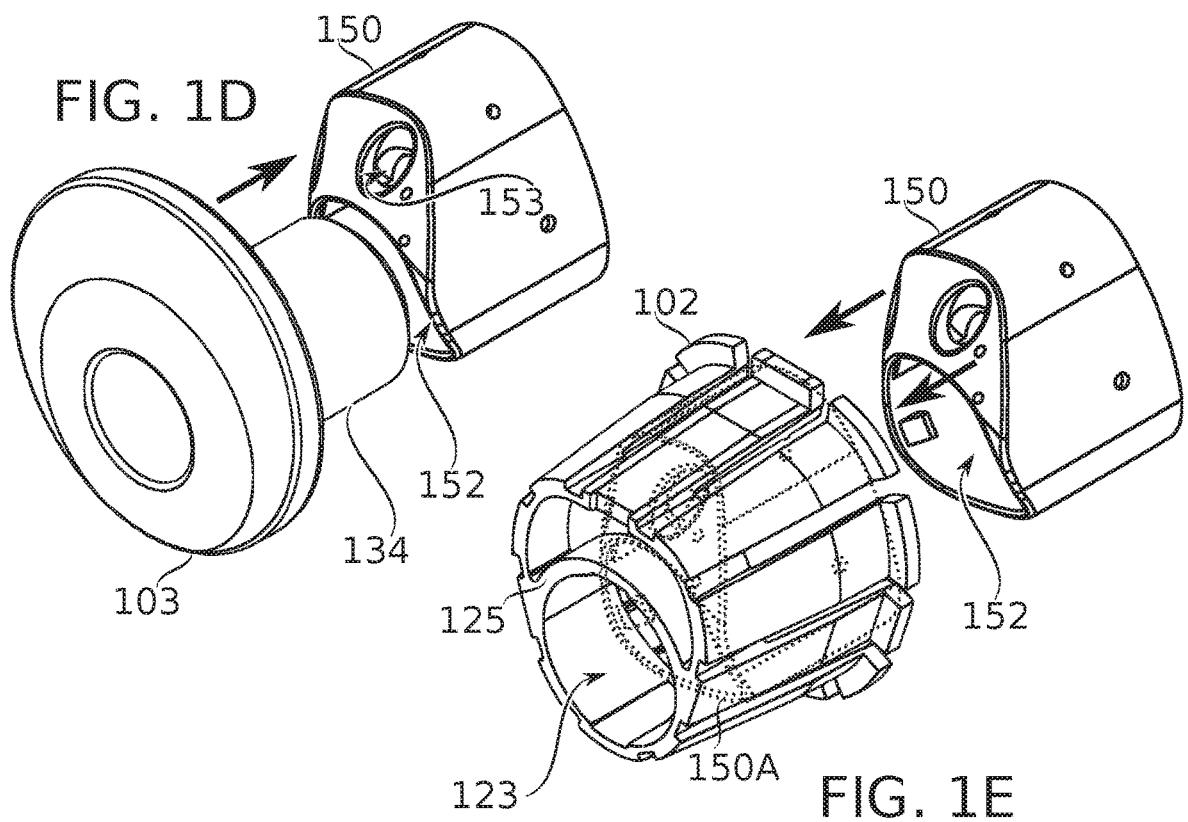
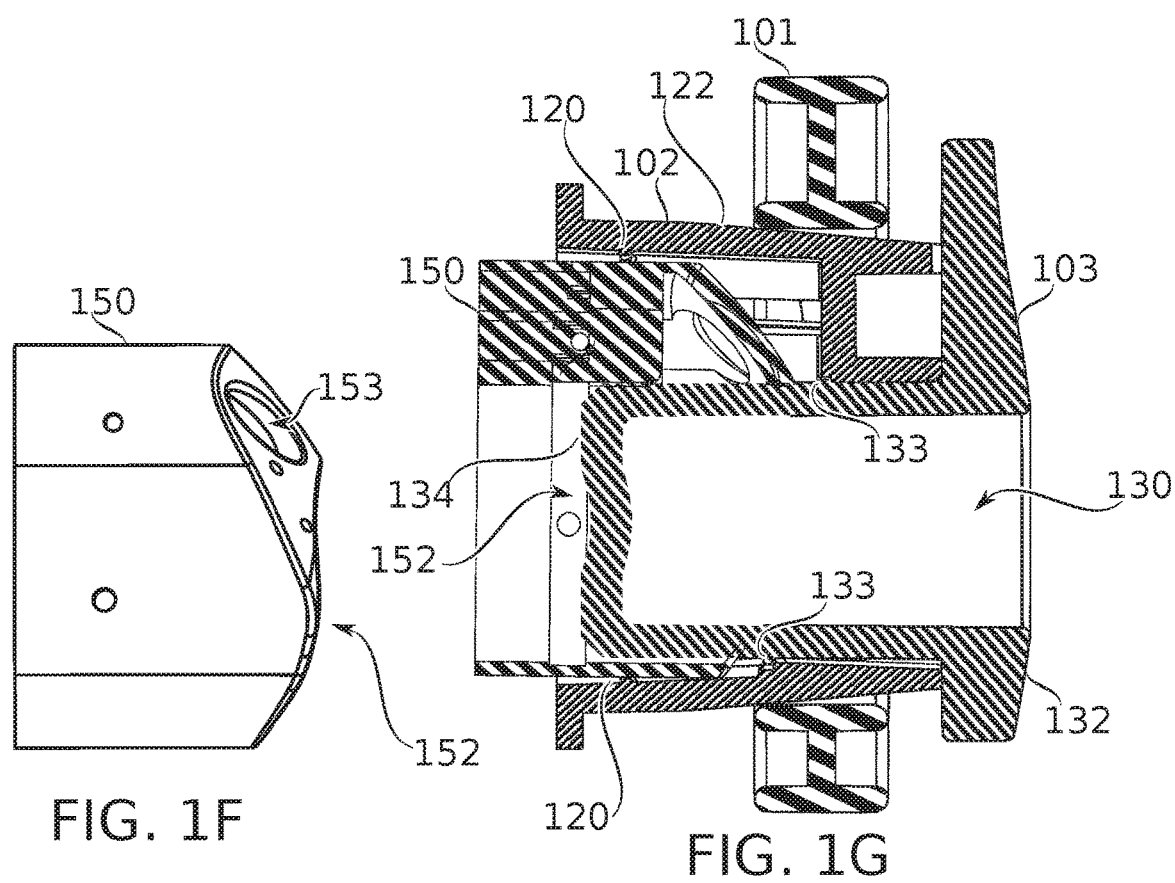

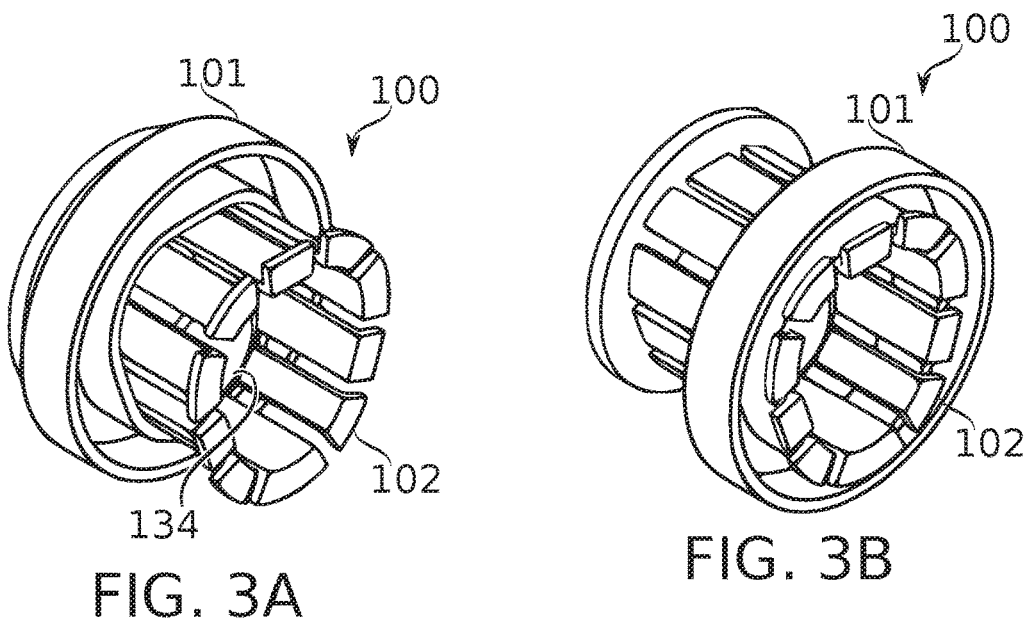
FIG. 3A
FIG. 3B
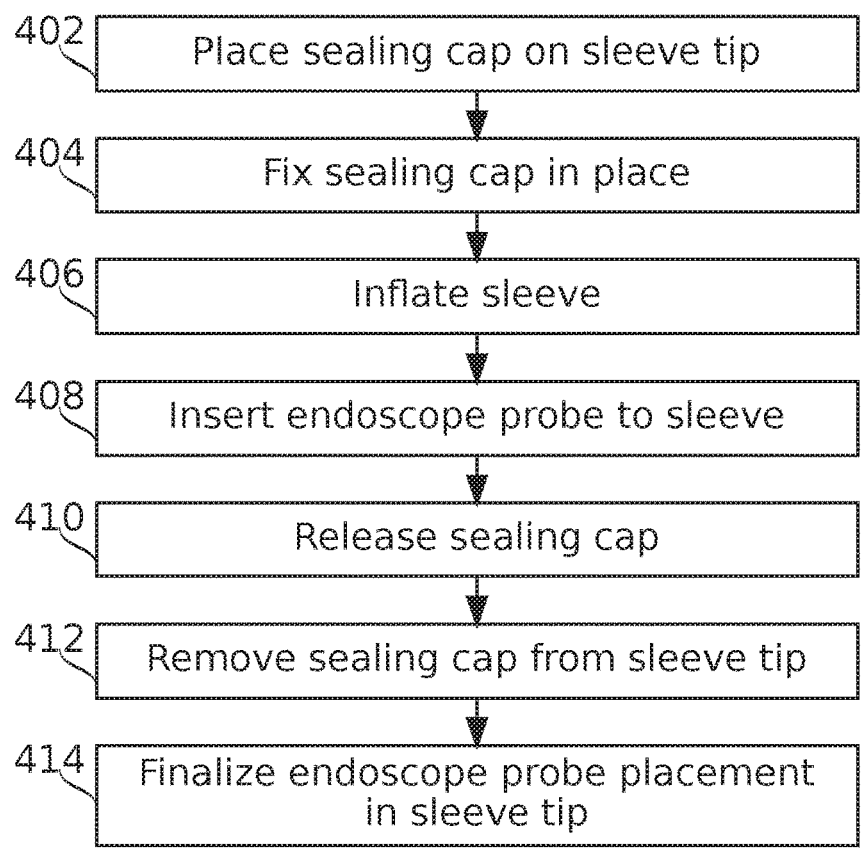
FIG. 4A

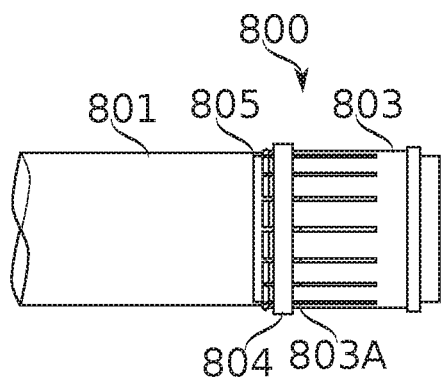 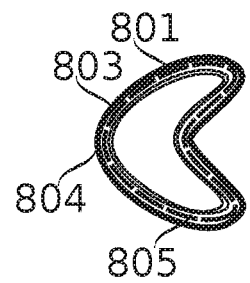
FIG. 8A                FIG. 8B
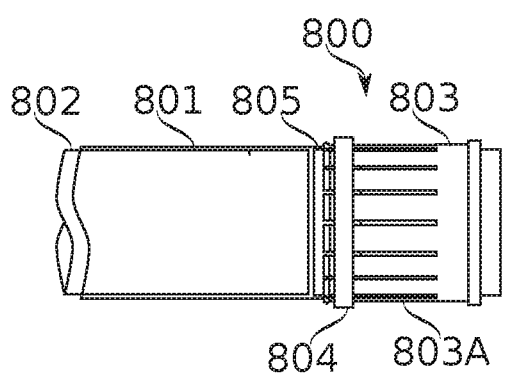 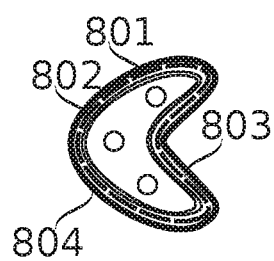
FIG. 8C                FIG. 8D
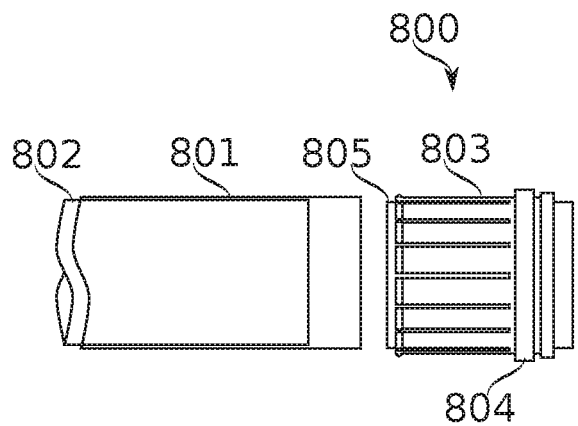 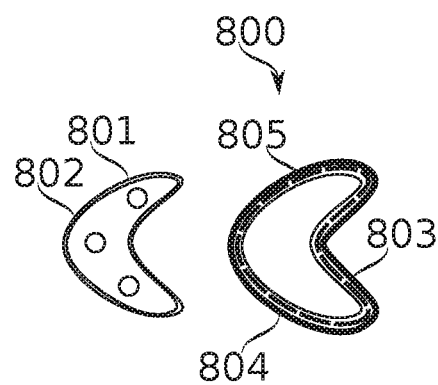
FIG. 8E                FIG. 8F

US 11,510,554 B1

PLUG FOR ENDOSCOPE ATTACHMENT TIP

RELATED APPLICATION

The present application claims the benefit of priority under 35 USC 119(e) of U.S. Provisional Patent Application No. 62/881,392 filed on Aug. 1, 2019, the contents of which are incorporated herein by reference.

FIELD AND BACKGROUND OF THE INVENTION

The present invention, in some embodiments thereof, relates to the field of endoscopic attachments; and more particularly, to methods of coupling between an endoscope and endoscopic attachments.

International Patent Publication No. WO2015/193896, filed Jun. 17, 2015, describes a sleeve assembly for coupling a colonoscope insertion tube to an add-on tube, in which an elongated lumen comprises an inner sleeve sized to receive an insertion tube of a colonoscope, an outer sleeve encircling the inner sleeve, and one or more add-on tubes positioned between the inner sleeve and the outer sleeve. The sleeve is expandable by inflation, and collapsible to fit tightly over a colonoscope insertion tube received within the inner sleeve.

SUMMARY OF THE INVENTION

There is provided, in accordance with some embodiments of the present disclosure, a method of inserting an endoscope to an endoscope sleeve, the method comprising: placing a corking body of a sealing cap into an aperture of the endoscope sleeve; latching the sealing cap onto the endoscope sleeve to secure the corking body within the aperture; inflating the endoscope sleeve; inserting an endoscope up to a distal portion of the endoscope sleeve; unlatching the sealing cap; and removing the corking body from the aperture.

In some embodiments, the latching comprises sliding a closure retainer along the sealing cap from an open-cap position to a closed-cap position.

In some embodiments, the latching comprises collapsing a plurality of tabs of the sealing cap surrounding a circumference of a distal tip of the endoscope sleeve onto the distal tip.

In some embodiments, the tabs surround a non-circular circumference of the distal tip.

In some embodiments, the collapsing comprises sliding a closure retainer along the tabs to press the tabs against the distal tip.

In some embodiments, the closure retainer comprises a non-circular inner circumference, and the non-circular inner circumference presses the tabs against the distal tip.

In some embodiments, the collapsing comprises sliding a closure retainer along the tabs, wherein a non-circular inner surface of the closure retainer compresses the tabs radially inward as it slides along the tabs; and wherein the tabs compress against the non-circular circumference of the endoscope sleeve distal tip.

In some embodiments, the non-circular circumferences are each roughly polygonal in a cross section, perpendicular to a longitudinal axis of the endoscope sleeve.

In some embodiments, engaging surfaces on the plurality of tabs comprise protrusions on the tabs which press into the distal tip when the tabs are collapsed onto the distal tip.

In some embodiments, an outer surface of the distal tip is soft, and yields to the engaging surfaces of the protrusions on the tabs.

In some embodiments, engaging surfaces on the plurality of tabs protrude radially inward proximally to the distal tip to secure the corking body within the aperture.

There is provided, in accordance with some embodiments of the present disclosure, a method of capping a distal tip of an endoscope sleeve, the method comprising: inserting a corking body to an aperture of the distal tip, wherein the corking body is attached to a tab body that surrounds a non-circular circumference of the distal tip; and collapsing tabs of the tab body onto the non-circular circumference of the distal tip.

In some embodiments, the collapsing tabs comprises sliding a closure retainer along the tab body to collapse the tabs onto the non-circular circumference of the distal tip.

There is provided, in accordance with some embodiments of the present disclosure, a sealing cap for sealing an end of an inflatable endoscope sleeve, the sealing cap comprising: a corking body, sized and shaped to insert to and seal an aperture of the end of the inflatable endoscope sleeve; a tab body, comprising flexible tabs arranged around a circumference of the corking body, and spaced sufficiently therefrom to allow insertion of the end of the inflatable endoscope sleeve; a closure retainer, surrounding the flexible tabs of the tab body, and configured to slide along a longitudinal extent of the corking body, compressing the tabs radially inward.

In some embodiments, an inner circumference of the closure retainer positioned to compress the tabs radially inward is non-circular.

In some embodiments, an outer circumference of the closure retainer is circular.

In some embodiments, the non-circular inner circumference is roughly polygonal.

In some embodiments, the non-circular inner circumference is roughly triangular.

In some embodiments, the corking body comprises an end-dimple, configured to buckle upon insertion of the corking body to an aperture of the end of the inflatable endoscope sleeve.

In some embodiments, the corking body is a portion of a sealing body, and the sealing body and the tab body are secured to each other by a snap fit.

In some embodiments, the tabs comprise protrusions which press into the distal tip when the tabs are collapsed onto the distal tip.

In some embodiments, the tabs comprise engaging surfaces configured to protrude radially inward proximally of the distal tip to secure the corking body within the aperture.

There is provided, in accordance with some embodiments of the present disclosure, a method of inserting a medical instrument to a protective sleeve, the method comprising: placing a corking body of a sealing cap into an aperture of the protective sleeve; latching the sealing cap onto the protective sleeve to secure the corking body within the aperture; inflating the protective sleeve; inserting the medical instrument up to a distal portion of the protective sleeve; unlatching the sealing cap; and removing the corking body from the aperture.

There is provided, in accordance with some embodiments of the present disclosure, a sealing cap for sealing an end of an inflatable protective sleeve of a medical instrument, the sealing cap comprising: a corking body, sized and shaped to insert to and seal an aperture of the end of the inflatable protective sleeve; a tab body, comprising flexible tabs arranged around a circumference of the corking body, and spaced sufficiently therefrom to allow insertion of the end of the inflatable protective sleeve; a closure retainer, surrounding the flexible tabs of the tab body, and configured to slide along a longitudinal extent of the corking body, compressing the tabs radially inward.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIGS. 1D-1G schematically illustrate details of the fitting of a sleeve tip to components of a sealing cap, according to some embodiments of the present disclosure;

FIGS. 3A-3B show sealing cap in cap-open and cap-closed configurations, respectively, according to some embodiments of the present disclosure;

FIG. 4A is a schematic flowchart of a method of using a sealing cap for insertion of an endoscope probe to an endoscope sleeve, according to some embodiments of the present disclosure;

FIGS. 8A-8F schematically illustrate a sleeve-placement guide cap, according to some embodiments of the present disclosure.

DESCRIPTION OF SPECIFIC EMBODIMENTS OF THE INVENTION

Figure 1A:
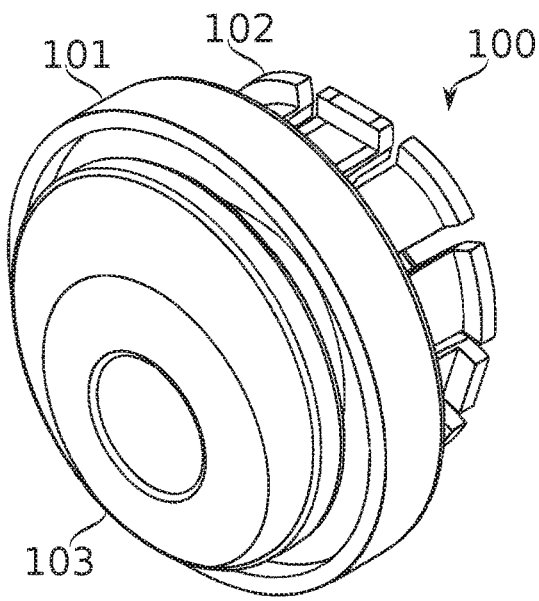
FIGS. 1A-1C schematically illustrate isometric (FIGS. 1A-1B) and cross-section (FIG. 1C) views of a sealing cap, according to some embodiments of the present disclosure.

The present invention, in some embodiments thereof, relates to the field of endoscopic attachments; and more particularly, to methods of coupling between an endoscope and endoscopic attachments.

Overview

An aspect of some embodiments of the present disclosure relates to a reversibly attachable pressure-resistant cap for an endoscope sleeve. The cap is configured, in some embodiments, to seal a distal tip of the endoscope sleeve during pressurized inflation of the sleeve to assist insertion of the endoscope into the sleeve. The cap is also configured to be easily removed from the distal tip after inflation is no longer needed.

Herein, the term "endoscope sleeve" refers to a covering for an endoscope, and in some embodiments more particularly a cover for a flexible endoscope (e.g., a colonoscope) having a flexible section which the sleeve covers, and which is much longer (e.g., 40x or longer) than its diameter. The sleeve extends from a distal end of the endoscope toward a basal end, potentially to a length of over a meter; e.g., at least 100 cm, 120 cm, 140 cm, 160 cm, 180 cm, 200 cm, or another length. The covered length of the endoscope includes what is referred to herein as the endoscope's "probe" (or at least a distal section thereof). The endoscope probe comprises the portion of the endoscope which is configured to be inserted to a body cavity such as a colon.

In use, the endoscope sleeve may perform functions including, for example, one or more of:

Preventing or reducing contamination of the endoscope.

Binding and/or routing external conduits and/or cabling along the endoscope probe.

Providing ports configured for material outlet, material intake, and/or sensing; particularly ports on a distal tip of the endoscope sleeve.

In some embodiments, the distal tip of the endoscope sleeve is a multifunctional component, with shape and/or materials of construction suitable to match. For example, material outlet ports may be shaped to include nozzles which allow fluid to be delivered as high energy jets, and/or positioned to direct fluid in particular directions. Material intake ports (which optionally operate by the application of reverse pressure), are optionally protected from causing suction damage to tissue by being provided with pressure shunting ports, and/or a shape and/or soft material construction which reduces a likelihood that tissue will be suctioned onto. The tip optionally includes sensors within the sensing ports. The sensor ports may be protected from ingress of material by any suitable combination of features such as size, covering, and/or orientation. Moreover, in some embodiments, the tip is shaped to attach to the endoscope without impeding its normal functions (e.g., viewing and/or tool delivery), and is optionally provided atraumatic features such as rounded-off surfaces and/or a soft (e.g., yielding in shape) outer material. The resulting tip shape is potentially quite complicated, irregular and/or subject to deformation by design; particularly compared to the typically circular cross-section of the distal endoscope portion by itself.

Moreover, in some embodiments of the present invention, endoscope sleeves used with the pressure-resistant cap are subjected during their use to a period of inflation, particularly inflation to assist in installing the endoscope sleeve over an endoscope with which it is to be used. This potentially assists dressing the endoscope with the sleeve, for example to help support efficient workflow in clinics which routinely perform endoscopic procedures. A method of accomplishing sleeve placement over the endoscope, in some embodiments, comprises inflation of the sleeve to a diameter slightly larger than the endoscope, insertion of the (optionally lubricated) endoscope, and then collapse of the sleeve onto the endoscope.

The distal tip of the endoscope sleeve may include one or more open apertures (from among its ports, for example) which must be sealed before inflation can happen—but after inflation, seals must also be removed so that the sleeved endoscope probe can be put into use.

The combination of an irregular, multifunctional tip and a need for sealing raises potential difficulties. Soft material of the sleeve tip results in a distal tip which is deformable and/or delicate. This potentially interferes with the ability to obtain reliable sealing; restricting how much force and/or where force may be safely applied in order to obtain sealing before inflation, and after inflation, to effect removal of the seal. Soft surfaces, in some embodiments, include surfaces of one or more apertures of the tip which must be sealed in order to allow sleeve inflation—but the soft surfaces may not be strong enough to resist pressure in the manner of a cork in a bottle neck. In some embodiments, it is optionally an object to avoid using sealing surfaces that intrude too deeply into the tip, so that an endoscope can be inserted more distally before deflation. However, shortening the sealing surfaces has the potential disadvantage of reducing the security of engagement under pressure.

A tip's irregular shape also potentially interferes with the use of general purpose securing mechanisms such as threading.

In some embodiments of the present disclosure, a sealing cap is provided which is specially shaped to provide tip sealing on some surfaces; and, separately, anchoring on other surfaces. These work together to create a pressure seal well-enough closed to allow inflation of the sleeve, and well-enough secured to ensure that the cap will not detach under the pressure of inflation.

In some embodiments, this shape includes engaging surfaces shaped and positioned to engage with the sleeve tip on portions of its outer circumference. The engaging surfaces are mounted on flexible tabs, for example, flexible tabs connected to a common tab body.

Optionally, the engaging surfaces of the tabs engage with corresponding structures of the sleeve tip, for example dimples on its outer circumference, or larger surfaces sloped or otherwise shaped to resist forward slipping of the sealing cap. In some embodiments, the engaging surfaces engage in a friction fit. In some embodiments, the engaging surfaces are configured to press down hard enough on the tip to create dimples deep enough to promote engagement of the sealing cap to the sleeve distal tip. In some embodiments, the sealing cap is shaped to include flange surfaces positioned to engage with the sleeve tip from a proximal side, so that distally-directed forces due to inflation serve to press the flanges more strongly against the sleeve tip.

In some embodiments, the sealing cap includes a corking body. In some embodiments, the corking body inserts from a distal side into one or more distally-oriented apertures of the tip in fluid communication with the pressurized fluid (typically air) used to inflate the sleeve. This allows the sleeve to be inflated. Although the facing surfaces of cork body and tip aperture may be configured to offer insufficiently reliable resistance to dislodging under pressure, they may nevertheless provide adequate sealing, so long as they are prevented from dislodging by some other holding force (e.g., as provided by interaction of the engaging surfaces with the proximal side of the sleeve's distal tip).

Furthermore, in some embodiments, the pressure-resistant cap is configured with an attachment latch allowing the cap to be attached and/or released from the distal tip quickly; without exerting large forces to be exerted, and/or while controlling the extent of forces exerted on surfaces of the sleeve tip itself. In some embodiments, the latch comprises a buckle, hasp, toggle, or closure retainer.

In particular, in some embodiments of the present disclosure, the attachment latch comprises a closure retainer, optionally in the shape of a circular or non-circular ring or clip), movable (e.g., by sliding) between a cap-open position and a cap-closed position. In the cap-open position, the closure retainer is positioned so that the tabs are forced and/or allowed to spread radially outward. When moved to the cap-closed position (e.g., by sliding the closure retainer along a distal-proximal axis of the cap body), the closure retainer forces the tabs radially inward, whereat (when the cap is already placed on the distal tip) the engaging surfaces are positioned to engage with the endoscope sleeve tip.

In some embodiments, radial movement of the tabs is facilitated by mounting them on a plurality of divided tabs, each of which extends longitudinally (e.g., over a distance of about 5-25 mm) from the tip-engaging tab surface to a fulcrum attaching them to the cap. The tabs, in some embodiments, are (for example) about 2-7 mm wide, separated by intervals of (for example) about 0.5-3 mm.

Such a mechanism makes use of leverage, allowing a relatively low longitudinal force exerted to translate the closure retainer longitudinally along the distal-proximal axis of the cap to produce a relatively large radial holding force by smaller movements of the tab. Furthermore, by holding the tabs radially inward, the closure retainer helps prevent radially outward movement of the tabs which might otherwise occur upon application of inflation force to the capped endoscope sleeve. Similarly, a relatively low longitudinal actuating force (compared to radial holding force) is required to release the cap. In some embodiments, the ratio of longitudinal force to radial holding force is at least 5:1, 10:1, 20:1, or another ratio. The radial distance of inward movement by the tabs is predetermined by the relative sizes of the tabs and tab body and the closure retainer; potentially preventing excessive force from being exerted on the distal tip when the closure retainer is operated.

In some embodiments, the radial distance of inward movement by the tabs is set to compress a portion of the tip itself onto the corking body. Accordingly, a sealing and/or holding strength of the corking body to the tip is potentially enhanced directly when the cap is put in a cap-closed configuration. In some embodiments, distances of deformation of the tip under compression are maintained within the elastic limits of the tip to avoid permanent deformation.

Optionally, the cap is sized and shaped so that the tabs of the closed cap exert relatively little direct force on the tip itself, until inflation begins to urge the corking body forward. At that stage, the tab surfaces begin take up increasing load, as necessary to counteract the forces exerted by inflation. The corking body remains sealing, however, e.g., because its surfaces are substantially parallel to surface of the aperture(s) it seals, and/or because it itself spreads slightly under longitudinal squeezing, enhancing the seal. In some embodiments, the ratio of inflated holding force to uninflated clamping force is at least 5:1, 10:1, 20:1, or another ratio.

Predetermined control of clamping by the sealing cap provides a potential advantage to avoid acute damage to the sleeve tip (e.g., cracking or marring of surface material), when the cap is placed on it, e.g., in preparation for inflation. Additionally or alternatively, in some embodiments, the cap is positioned open or closed on the sleeve during a long-term period of storage (for example, closed as part of device packaging during manufacture). It is a potential advantage during this period for the cap to be exerting forces on the tip which are too low to create permanent (e.g., plastic) deformation of the tip's shape.

It is noted in particular that in some embodiments a sleeve tip may include nozzles for the directing of fluid jets manufactured to functioning tolerances which could be violated if the nozzles became squeezed and/or redirected due to pressures exerted when the cap is attached, either in preparation for use; or over a period of storage, for example, 1-6 months of storage.

Wide distribution of holding force across surface of the sleeve tip is also a potential advantage for avoiding sleeve tip damage while maintaining a pressure-resistant seal. In some embodiments, the tab surfaces engage with the sleeve tip around a full circumference of the sleeve tip, optionally interrupted at intervals of about 2-7 mm by gaps comprising 20% or less of the overall circumference. Additionally or alternatively, in some embodiments, locations on the sleeve tip engaged by the sealing cap are strengthened. For example, the tip may include extra reinforcing material near locations of contact, and/or exposed "islands" of harder material surrounded by softer surface material at locations where the engaging surfaces of the sealing cap make contact.

While embodiments of the present disclosure are described in terms of and using the example of a sealing cap for an endoscope sleeve, it should be understood that the sealing cap, in some embodiments, is adapted for use with a protective sleeve suited to use in covering any reusable medical instrument wherein the sleeve—with a locked cap plugging its distal end—is inflated to allow insertion of the medical instrument, collapsed, and then the cap unlocked and removed from an end of the sleeve to expose the medical instrument from that end. Examples of such reusable medical instruments include, in some embodiments, endoscopes generally (for example as described in examples herein); more particular endoscope types including colonoscopes, gastroscopes, and/or laparoscopes; and devices such as ultrasound transducers, lasers, and other sensors and/or energy delivery devices and/or their cabling. In some embodiments, the protective sleeve is used as a protective layer for use with hosing and/or electronic cabling. In some embodiments, the protective sleeve is used as a protective layer of the shaft of an instrument comprising a relatively large or irregular distal end (e.g., an end comprising a sensor or tool). Inflating the sleeve potentially eases passage of the distal end through the sleeve; upon release of inflation, the sleeve collapses onto the shaft. Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Sealing Cap Structure and Components

Figure 1B:
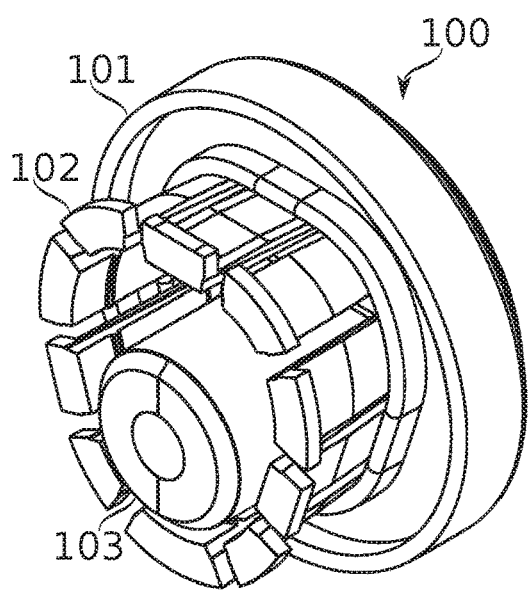
Figure 1C:
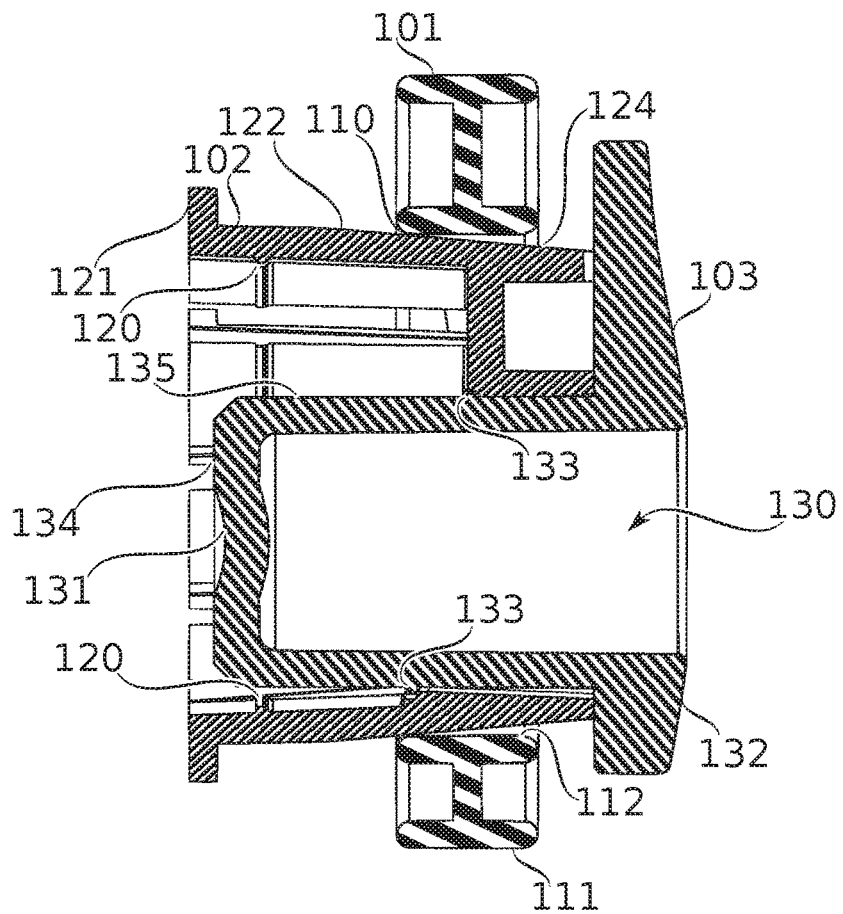
Figure 2A:
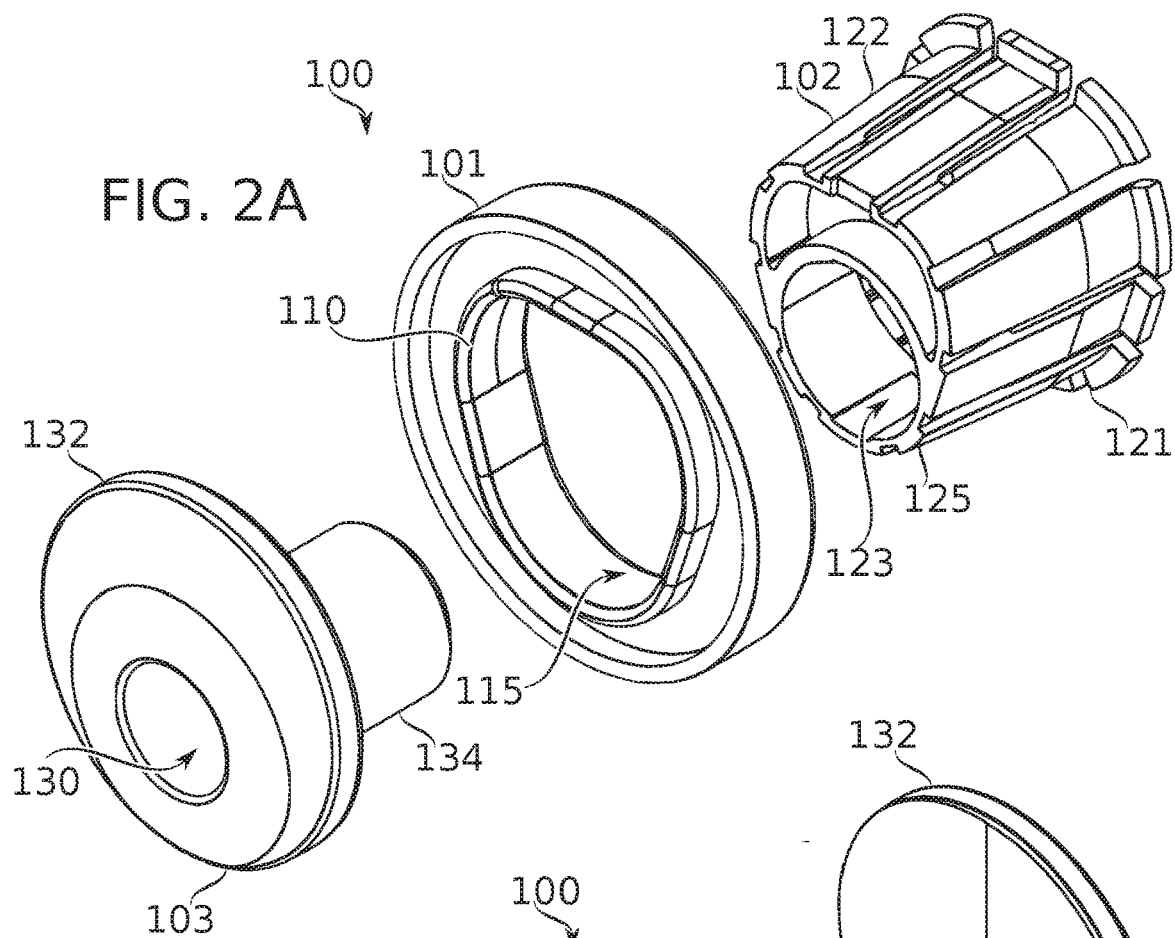
FIGS. 2A-2B show disassembled views of the components of a sealing cap, according to some embodiments of the present disclosure.
Figure 2B:
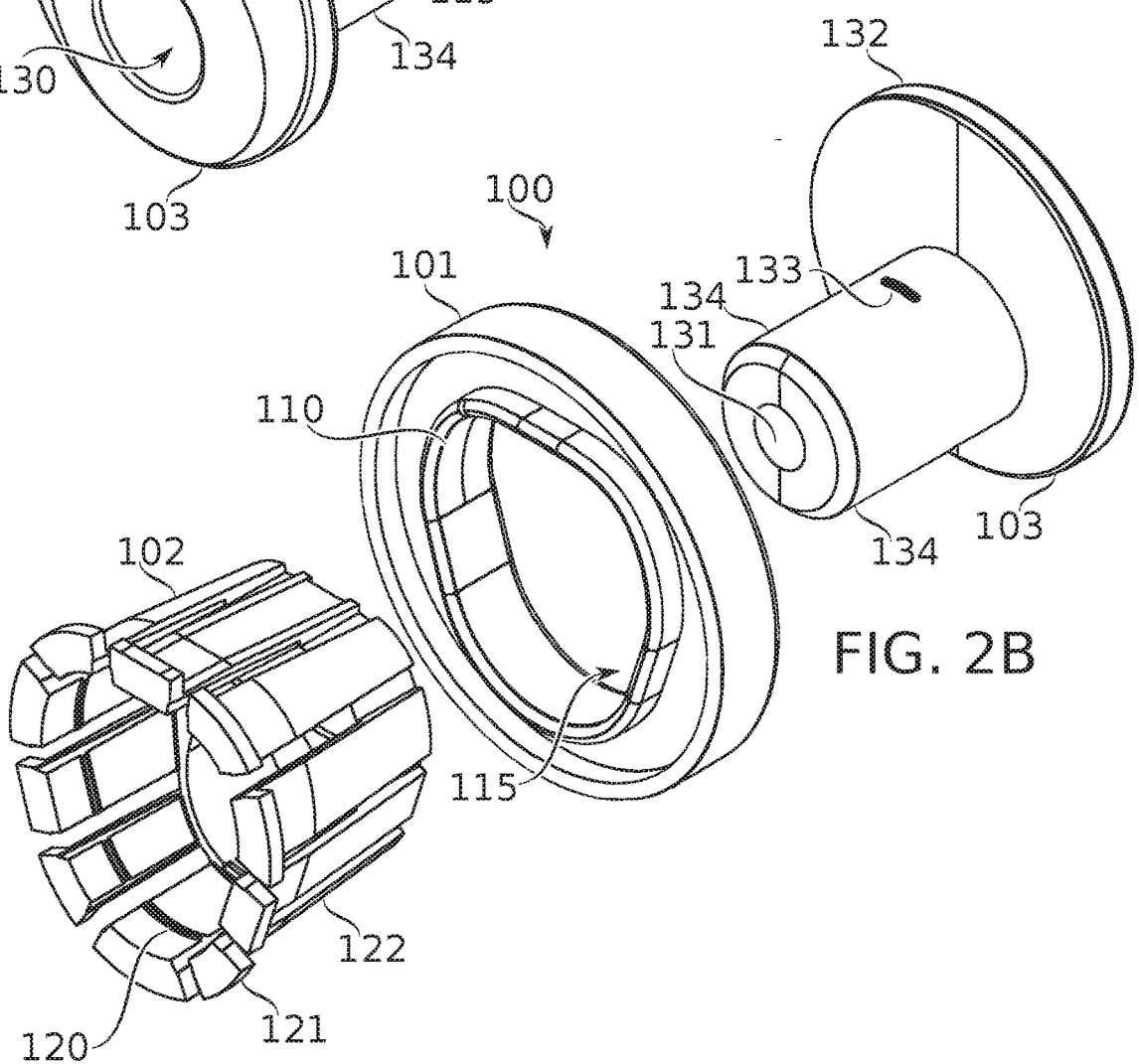

Reference is now made to FIGS. 1A-1C, which schematically illustrate isometric (FIGS. 1A-1B) and cross-section (FIG. 1C) views of a sealing cap 100, according to some embodiments of the present disclosure. For clarity, some features are provided with reference character labels just on the cross-section view of FIG. 1C. Reference is also made to FIGS. 2A-2B, which show disassembled views of the components of a sealing cap 100, according to some embodiments of the present disclosure.

In some embodiments, primary components of sealing cap 100 comprise sealing body 103, tab body 102, and closure retainer 101. FIG. 1A shows assembled sealing cap 100 from a distal side (in the open-cap configuration), and FIG. 1B shows assembled sealing cap 100 from a proximal side in the open-cap configuration. In the embodiment shown, the distal tip to be accommodated may have a polygonal or roughly polygonal (e.g., roughly triangular) cross-section (cross-section perpendicular to a longitudinal axis of the extended endoscope sleeve), sized to fit within the inner perimeter defined by tabs 122 of tab body 102. In some embodiments, the tip cross-section comprises another non-circular shape. The shape is potentially unsuited to clamping by a screw-on cap, since it lacks rotational symmetry.

In some embodiments a "roughly polygonal" shape has at least three straight or nearly straight section (e.g., radius of curvature at least 5x larger than the shape itself), joined to each other by corner regions. The corner regions are not necessarily sharp corners. Furthermore, "roughly triangular" refers to a three-sided shape of this type, "roughly quadrilateral" to a four-sided shape of this type, "roughly pentagonal" to a five-sided shape of this type, and so on. While roughly triangular configurations are shown as examples, herein, it should be understood that the cap is adaptable, in some embodiments, to other shapes; as may be suitable given a particular design for a distal tip of a particular endoscope sleeve.

Corking body 134 of sealing body 103 inserts within an aperture of the tip. The relationship between sealing cap 100 and a sleeve tip 150 is detailed further, for example, in relation to FIGS. 1D-1G.

Sealing body 103 comprises corking body 134, and optionally a faceplate 132. Optionally, engagement surfaces 133 (e.g., on corking body 134) engage tab body 102 (snap fit) with enough strength to resist blowing out under pressure. In some embodiments, tab body 102 and sealing body 103 are bonded to each other (e.g., by welding and/or glue) and/or secured with a separate fastener such as a peg, clip and/or screw. Optionally tab body 102 and sealing body 103 are manufactured as an integral piece. Separate manufacture facilitates use of different material for each component— e.g., a silicone rubber for sealing body 103 and a rigid polymer such as PTFE (polytetrafluoroethylene) or HDPE (high density polyethylene) for tab body 102 manufacture facilitates assembly of closure retainer 101 over tab body 102, while still allowing faceplate 152 to act as a stopper that limits distal travel of closure retainer 101. Optionally, the whole cap is made of a same material, for example HDPE.

In some embodiments, corking body 134 comprises a hollow 130 surrounded by a wall 135. In some embodiments, corking body 134 comprises an end-dimple 131—a curved section of wall 135 centered on the face of the deep end of hollow 130. End-dimple 131 potentially helps to absorb compressive forces when by buckling slightly corking body is inserted to an aperture, helping to maintain circumferential uniformity (and sealing). Herein, circular cross-section embodiments of corking body 134 are shown as examples. However, it should be understood that the design is not limited to circular shapes which insert to and seal circular apertures. Other cross-sectional shapes (e.g., roughly polygonal cross-sectional shapes; shapes comprising more than one corking body protrusion) are optionally used in some embodiments, appropriate to the shape(s) of aperture(s) of the distal tip of the endoscope sleeve which are to be sealed.

Tab body 102 comprises tabs 122, arranged around a circumference sized and shaped to accommodate a sleeve tip (e.g., including being spaced sufficiently from the corking body to allow a distal tip of an endoscope sleeve to be inserted therebetween), and attached to a base 124 of the tab body 102. In some embodiments, one or more of the tabs 122 comprises a stopper flange 121, which limits proximal travel of closure retainer 101. In some embodiments, tabs 122 include engaging surface 120 (e.g., a protruding bead), sized and positioned to engage with a sleeve tip in the cap-closed configuration.

Closure retainer 101 comprises an outer circumference 111, and an inner circumference 112. Inner circumference 112 is sized to fit over a circumference defined by tabs 122. As closure retainer 101 moves proximally over tab body 102, a contact area 110 on inner circumference 112 presses against tabs 122, compressing them radially inward (i.e., collapsing them; or in alternative and equivalent terms, confining them to more radially inward positions).

Use of an Endoscope Sleeve Tip Sealing Cap

Figure 4B:
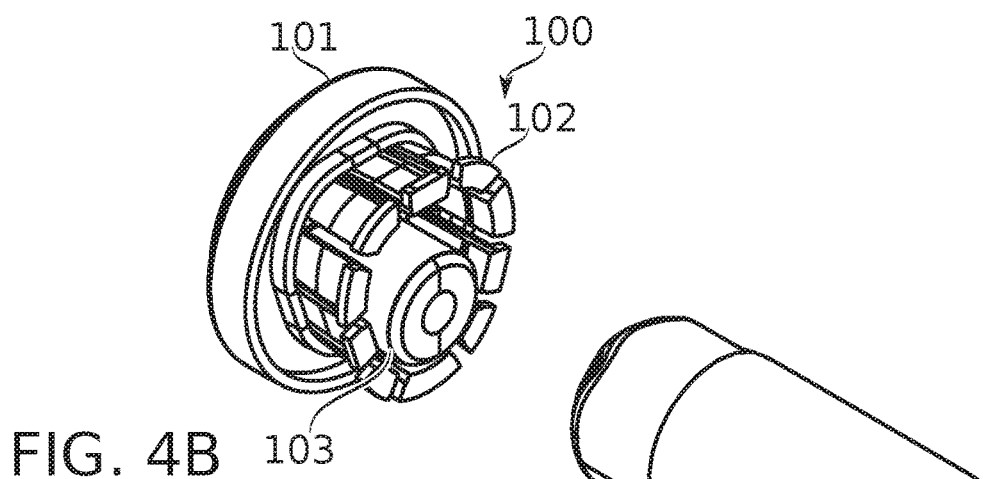
FIGS. 4B-4D schematically illustrate stages in assembly of a sleeve and sleeve tip with sealing cap, according to some embodiments of the present disclosure.

Reference is now made to FIG. 4A, which is a schematic flowchart of a method of using a sealing cap 100 for insertion of an endoscope probe 170 to an endoscope sleeve 212, according to some embodiments of the present disclosure. Further reference is made to FIGS. 4B-4D, which schematically illustrate stages in assembly of a sleeve 212 and sleeve tip 150 with sealing cap 100, according to some embodiments of the present disclosure. Additional reference is made to FIGS. 1D-1G, which schematically illustrate details of the fitting of a sleeve tip 150 to components of a sealing cap 100, according to some embodiments of the present disclosure.

Figure 4C:
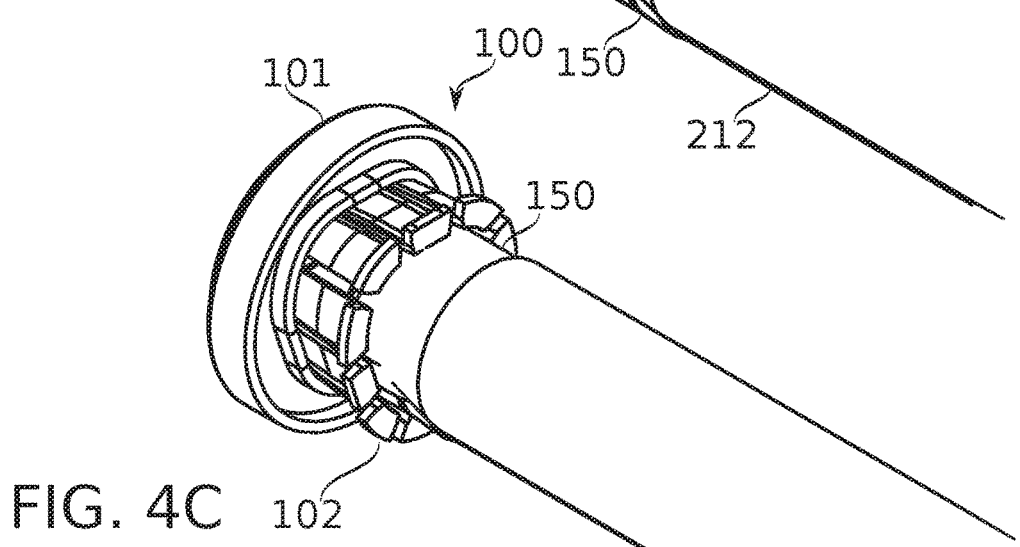

The flowchart begins, and at block 402, in some embodiments, a sealing cap 100 in the open-cap configuration is placed upon a tip 150 of an endoscope sleeve 212. FIGS. 4B-4C show approach (FIG. 4B) and placement (FIG. 4C) of the sealing cap.

Further details of the fitting of sealing cap 100 to tip 150 are shown in FIGS. 1D-1G. In FIG. 1D, sleeve tip 150 is shown with just the sealing body 103. Corking body 134 of sealing body 103 is sized to insert into and seal aperture 152 of sleeve tip 150. Aperture 152, in some embodiments, is the aperture into which a distal end of a colonoscope is fitted. Evacuation port 153, in some embodiments, is an example of an aperture which is not sealed by sealing body 103—it is normally pre-attached to an evacuation tube or otherwise configured so that it is not in fluid communication with the pressurized fluid used to inflate the sleeve 212. The arrow indicates the direction of movement of sealing body 103 as corking body 134 inserts into aperture 152.

In some embodiments, a sealing cap 100 comprises just sealing body 103. Although this arrangement is potentially less secure in resisting expulsion of the corking body under pressure, it optionally may be held in place, e.g., by hand pressure.

In FIG. 1E, sleeve tip 150 is shown with just tab body 102. Arrows indicate the direction of motion for inserting sleeve tip 150 with the circumference of the tabs 122. Upon insertion, apertures 123 and 152 are aligned, so that corking body 134 inserts first through aperture 123 and then into aperture 152. In some embodiments, corking body 103 couples to tab body 102 by engagement surfaces 133 pressing against the wall 125 of aperture 123.

Dotted outline 150A indicates a position of sleeve tip 150 when seated within tab body 102.

FIG. 1F shows sleeve tip 150 in profile, including indication of the relative positions of aperture 152 and an aperture 153. The cross-section of FIG. 1F corresponds to the configuration of FIG. 4B.

The sleeve tip profile of FIG. 1F is shown in cutaway in FIG. 1G, with the sleeve tip 150 inserted within the circumference of tabs 122, and engaging surfaces 120 poised to be compressed against it (equivalently: collapsed onto it) by a proximal movement of closure retainer 101. Corking body 134 is fitted within aperture 152. Optionally, corking body 134 inserts into sleeve tip 150 proximally past the point to which an endoscope is to be later advanced.

Continuing with FIG. 4A: at block 404, in some embodiments, the sealing cap is fixed in place. In the illustrated examples, this comprises proximal movement of closure retainer 101.

Figure 4D:
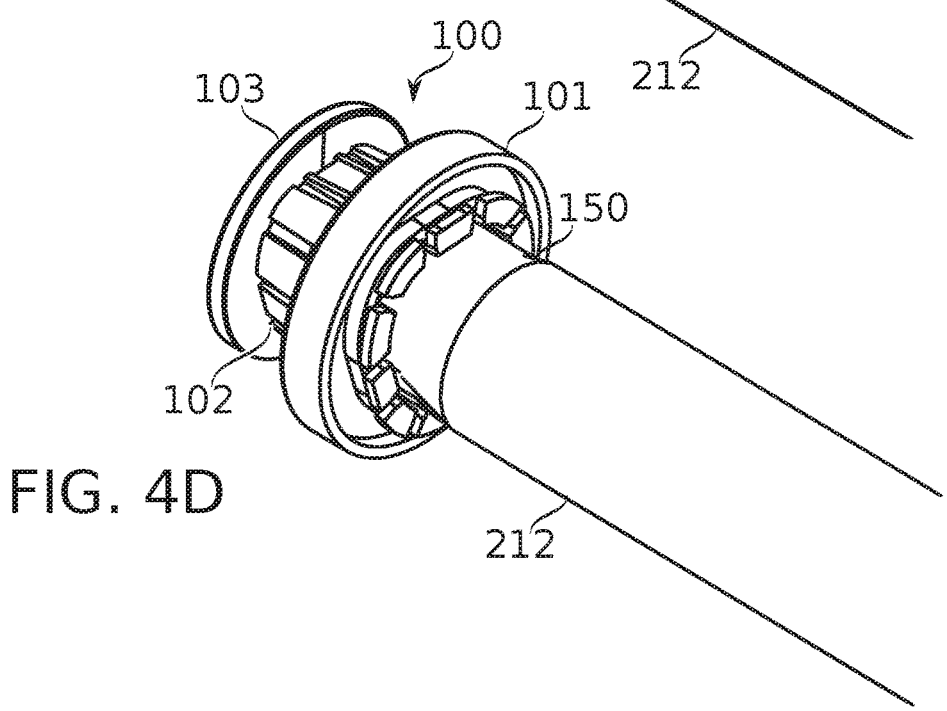

Reference is made to FIGS. 3A-3B, which show sealing cap 100 in cap-open and cap-closed configurations, respectively, according to some embodiments of the present disclosure. It should be noted that the sealing cap of FIGS. 3A-3B illustrates a design modified from that, e.g., of FIGS. 1A-1C: corking body 134 is relatively shorter. This potentially allows further advance of the endoscope probe 170 into it. FIG. 4D illustrates sealing cap 100 in a closed-cap configuration attached to tip 150 of endoscope sleeve 212.

In some embodiments, fixation of the cap comprises use of a different mechanism, for example, actuation of a latch and/or placement of an elastic band which holds the tabs in compression.

In some embodiments, fixation of the sealing cap is by latching the cap onto the endoscope sleeve, for example, fastening the cap with a lock, latch, and/or other element configured for securing the cap to the endoscope sleeve.

At block 406, in some embodiments, the sleeve is inflated, e.g., by introduction of pressurized fluid (typically air) from a proximal end of the sleeve. Since the sleeve is now sealed on its distal end by sealing cap 100, the sleeve inflates.

At block 408, in some embodiments, endoscope probe 170 is introduced into the inflated sleeve (e.g., through a valve at a proximal side of the sleeve), optionally after lubrication of the endoscope probe 170. Endoscope probe 170 is advanced until it reaches the end of the sleeve.

Figure 5A:
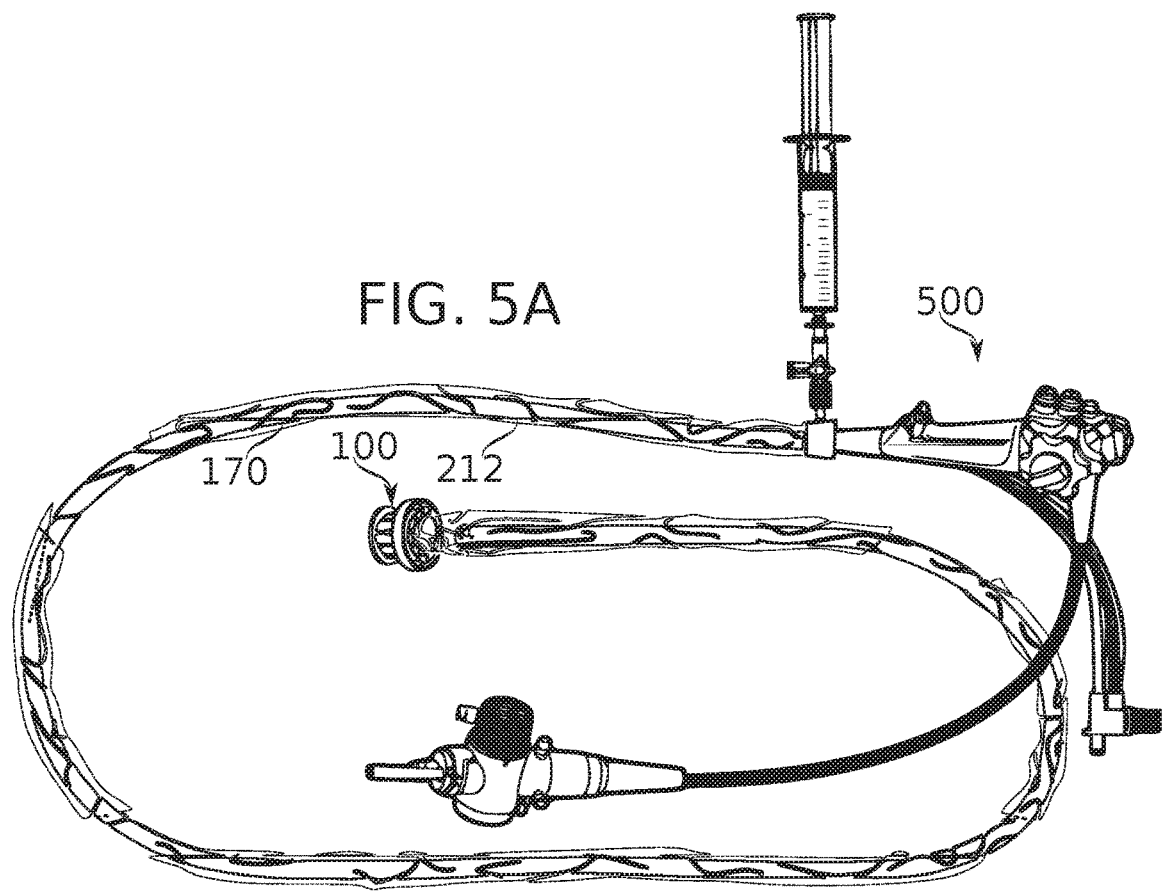
FIGS. 5A-5B show an overall view of an endoscope sleeve, into which an endoscope probe of an endoscope is inserted; and with a sealing cap attached to a distal tip of the endoscope sleeve, according to some embodiments of the present disclosure.
Figure 5B:
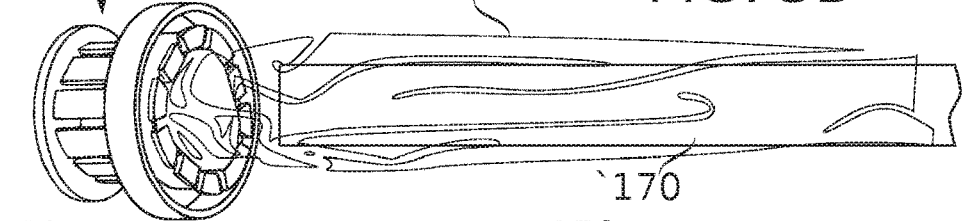

Reference is now made to FIGS. 5A-5B, which show an overall view of an endoscope sleeve 212, into which an endoscope probe 170 of an endoscope 500 is inserted; and with a sealing cap 100 attached to a distal tip of the endoscope sleeve 212, according to some embodiments of the present disclosure. In the position shown in FIGS. 5A-5B, endoscope probe 170 has not yet entered distal tip 150.

Figure 1H:
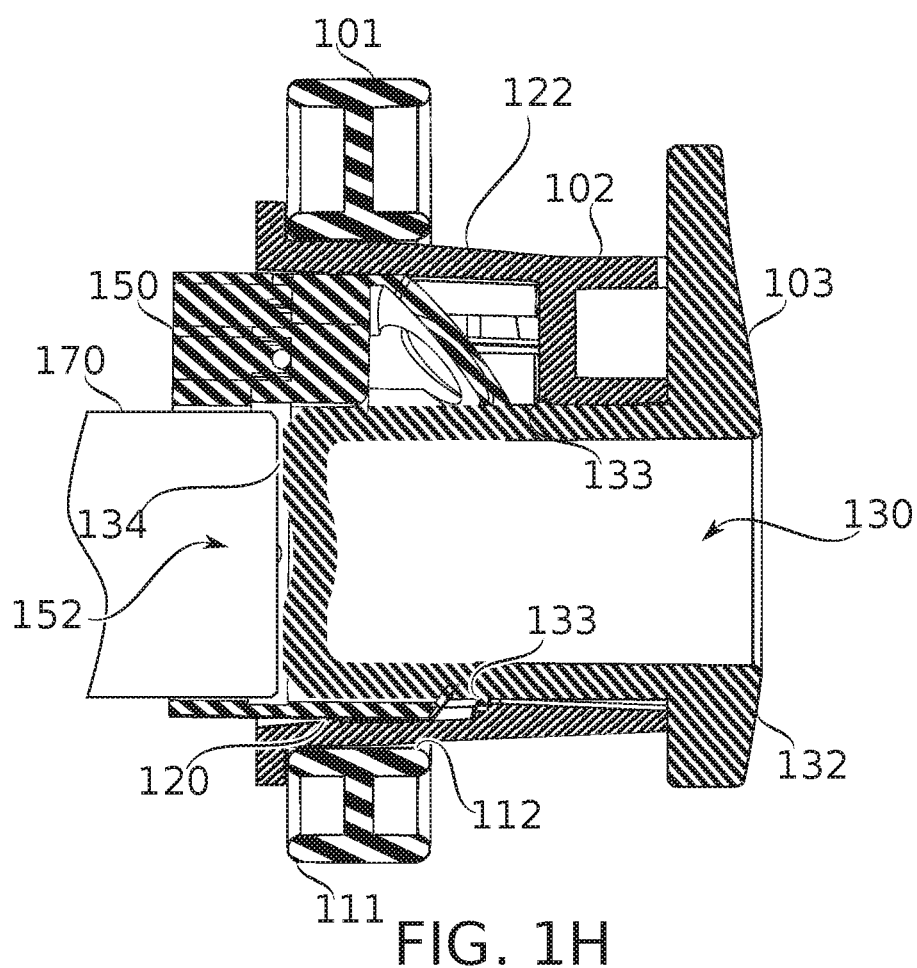
FIG. 1H schematically illustrate details of the fitting of a sleeve tip to components of a sealing cap in a closed-cap configuration along with an inserted portion of an endoscope probe, according to some embodiments of the present disclosure.

Reference is made to FIG. 1H, which schematically illustrate details of the fitting of a sleeve tip 150 to components of a sealing cap 100 in a closed-cap configuration along with an inserted portion of an endoscope probe 170, according to some embodiments of the present disclosure. In the cross-section of FIG. 1H, endoscope probe 170 is shown fully advanced against corking body 134. Closure retainer 101 is still in the proximal (cap-closed) position, clamping tabs 122 onto sleeve tip 150.

At block 410, in some embodiments, the sealing cap 100 is released by movement of closure retainer distally. This is optionally preceded by release of inflation pressure from the endoscope sleeve 212 and subsequent deflation. At block 412, the sealing cap 100 is removed from the sleeve tip 150. In some embodiments, removing of the sealing cap is by unlatching the cap the from the endoscope sleeve, for example, by releasing a latching or locking element which couples the cap to the sleeve.

At block 414, in some embodiments, placement of the endoscope probe 170 in the sleeve tip 150 is finalized.

Figures 5C, 5D:
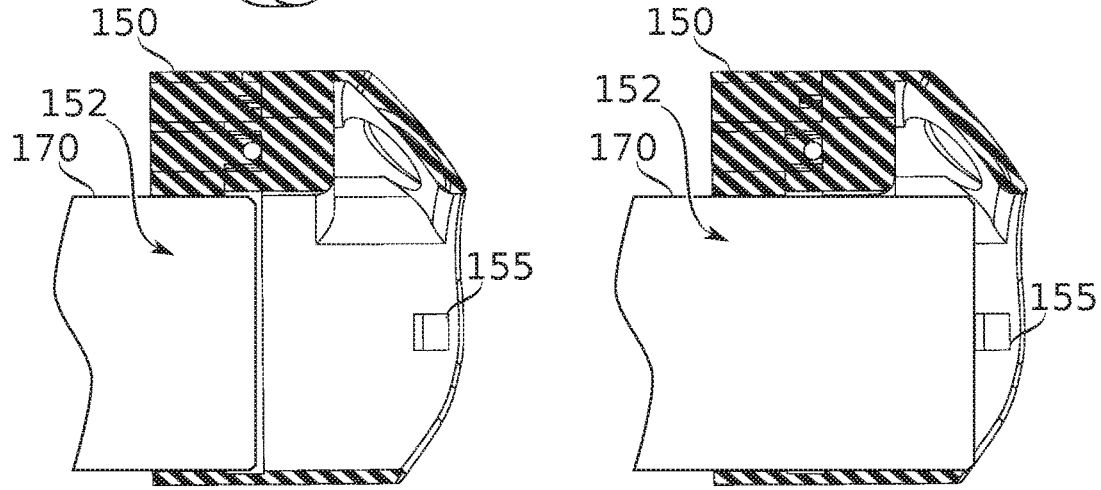
FIGS. 5C-5D schematically illustrate final positioning of an endoscope sleeve tip sealing cap, according to some embodiments of the present disclosure.

Reference is made to FIGS. 5C-5D, which schematically illustrate final positioning of an endoscope sleeve tip 150 sealing cap 100, according to some embodiments of the present disclosure. Upon insertion to a sleeve 212, the distal-most position of endoscope probe 170 within aperture 152 of sleeve tip 150 is, in some embodiments, initially limited by the proximal side of corking body 134 (e.g., as shown in FIG. 1H). From this configuration, the sealing cap 100 can be removed, potentially allowing the inflated sleeve 212 to deflate, but leaving endoscope probe 170 slightly out of position (as shown in FIG. 5C). There remains some freedom of motion (i.e., due to the flexibility of the sleeve 212 permitting a certain amount of longitudinal compression). This allows pressing sleeve tip 150 proximally over endoscope probe 170 to its fully inserted position, e.g., so that a distal end of endoscope probe 170 seats against stop 155 as shown in FIG. 5D.

Further Examples

Back-locking Cap

Figure 6A:
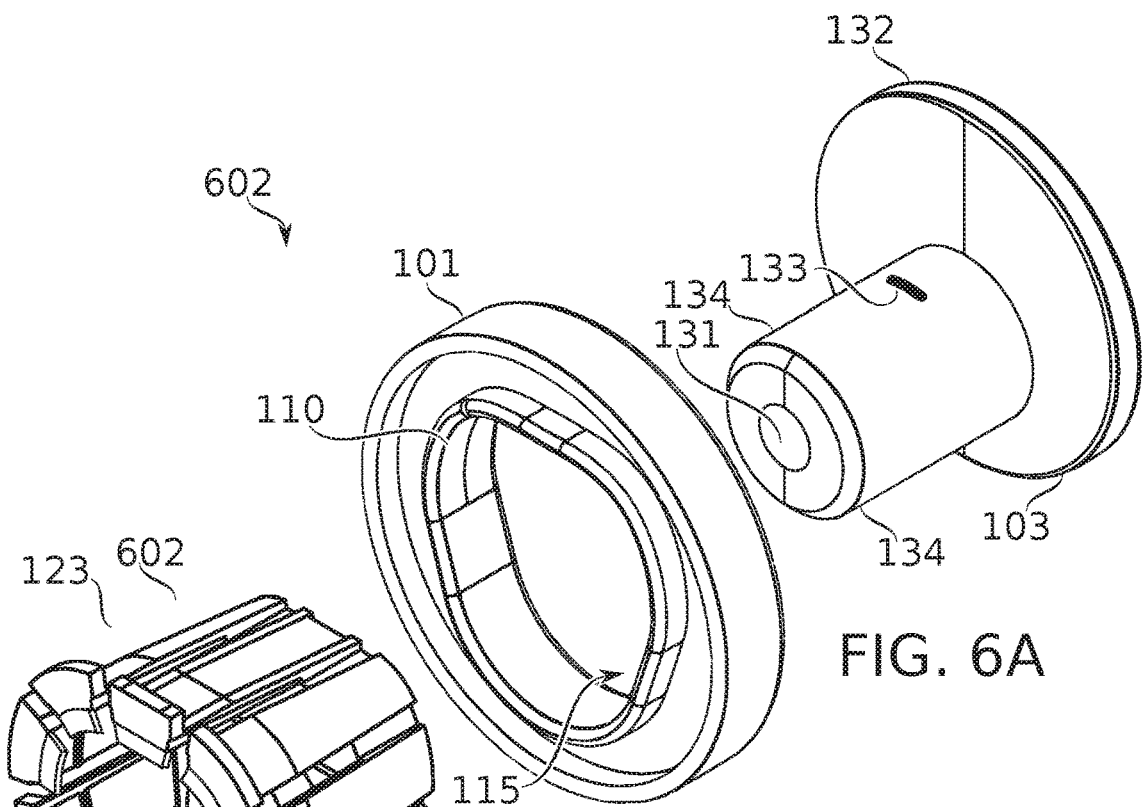
FIG. 6A schematically illustrates a disassembled view of a sealing cap comprising back-clamping flanges, according to some embodiment of the present disclosure.
Figure 6B:
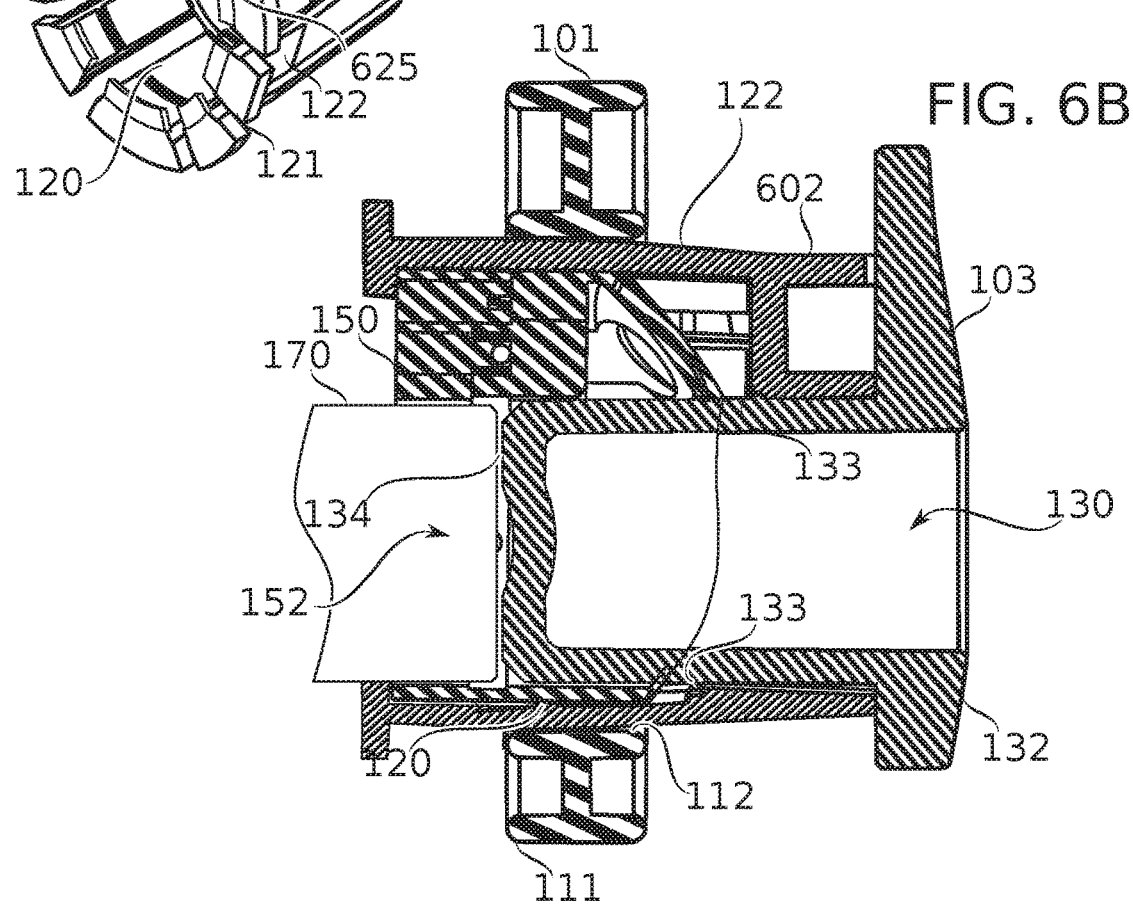
FIG. 6B schematically illustrates a cross-sectional view of the sealing cap, according to some embodiment of the present disclosure.

Reference is now made to FIG. 6A, which schematically illustrates a disassembled view of a sealing cap 600 comprising back-clamping flanges 625, according to some embodiment of the present disclosure. Reference is also made to FIGS. 6B, which schematically illustrates a cross-sectional view of the sealing cap, according to some embodiment of the present disclosure.

In some embodiments, additional holding security is provided to a sealing cap 600 by inward-directed flanges 625, positioned on a proximal side of tab body 602 (components of tab body 602 otherwise correspond to those of tab body 102, in some embodiments). The tabs are sized so that when a distal tip 150 is inserted, flanges 625 close behind distal tip 150 (e.g., as shown), and/or insert into and/or behind engaging surfaces of distal tip 150.

Components 103 and 101 (and their sub-elements) are optionally the same in design as components 103 and 101 of sealing cap 100.

Low Profile Sleeve-End Locking Cap

Reference is now made to FIGS. 7A-7H, which schematically illustrate views of a locking cap 700 in the process of locking onto an end of a sleeve 702 in place on a medical instrument 702, according to some embodiments of the present disclosure.

Figure 7A:
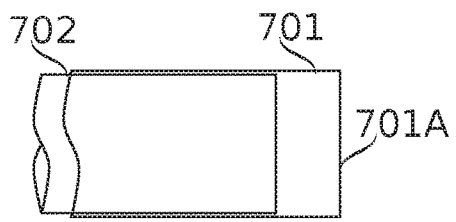
FIGS. 7A-7H schematically illustrate views of a locking cap in the process of locking onto an end of a sleeve in place on a medical instrument, according to some embodiments of the present disclosure.
Figure 7B:
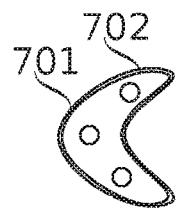

FIG. 7A shows a sleeve 701 covering a portion of a medical instrument 702; for example an endoscope. Optionally a distal end 701A of the sleeve is provided without an integral tip. FIG. 7B shows an end-on (from the distal end) view of medical instrument 702 and sleeve 701, illustrating a non-circular cross-sectional profile. The profile in the example shown also comprises a concavity. This poses a potential problem for a sleeve end, which might tend to "flop open" if left unsecured. In any case, advance of the enslaved medical instrument within a body cavity might tend to push back the sleeve if left unsecured.

Alternatively, in some embodiments, the profile periphery is convex, and shape suitable for the functions of medical instrument 702; not necessarily circular.

Locking cap 700 provides a low profile tip which is configured to be locked onto the sleeve's free (e.g., distal) end and hold it into place.

Figure 7C:
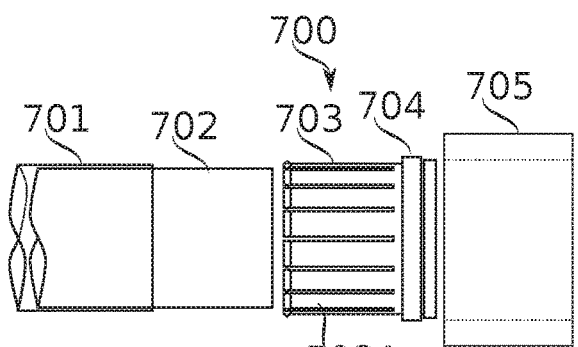
Figure 7D:
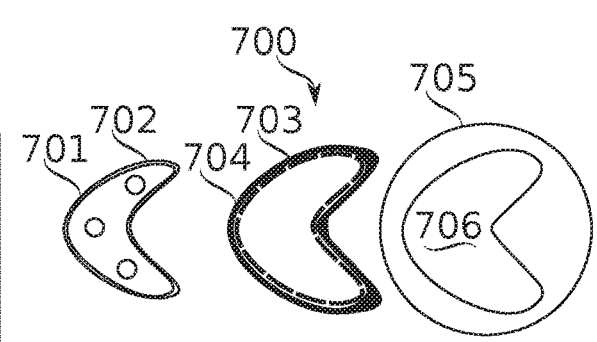

In FIG. 7C, medical instrument 702 has been advanced out of sleeve 701, and is positioned ready to receive locking cap 700. Locking cap 700 comprises flange body 703 and closure retainer 704. In some embodiments, closure retainer 704 comprises a band of metal and/or polymer; for example a nitinol band which is superelastically set to a shape which acts to exert compressive force on flanges 703A when it moves over them. In some embodiments, selected positions of closure retainer 704 are reinforced to help it hold its shape, for example, at selected corners. Optionally, flange body 703 is open-ended, e.g., to allow instrumentation and/or ports of medical instrument 702 free forward access. Optionally, flange body 703 is at least partially closed-ended, e.g., closed over with a transparent window.

When locking cap 700 is fully seated (as in FIG. 7E), sliding closure retainer 704 along flange body 703 acts to exert radially compressing forces on flanges 703A, which in turn causes locking cap 700 to lock onto both the end of the sleeve 701 and the medical instrument 702.

In some embodiments, closure retainer 704 is low profile, e.g., protruding less than 2 mm from the surface of flange body 703. This low profile may be difficult to manipulate by fingers alone. In some embodiments, a locking tool 705 is provided, sized to fit over the end of locking cap 703, but still fitting tightly enough to contact closure retainer 704, allowing the closure retainer 704 to be moved into the locking position (e.g., advanced distally) by manipulation of locking tool 705, which is potentially easier to grip and exert force on. FIG. 7D again shows the cross-sectional profiles of sleeve 701 and medical instrument 702; separately shown is a corresponding cross-sectional profile of flange body 703 (inner dotted line) and closure retainer 704 (outer solid line). Lumen 706 of locking tool 705 is sized to pass onto the end of flange body 703, while still being enough smaller than closure retainer 704 that locking tool 705 causes closure retainer 704 to be forced along the flanges 703A as locking tool 705 is advanced.

Figure 7E:
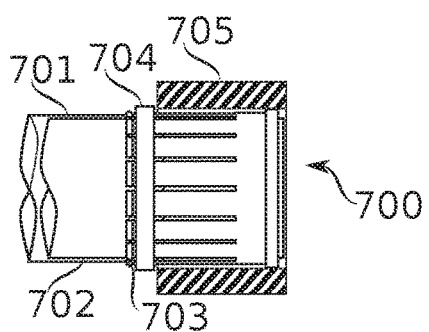
Figure 7F:
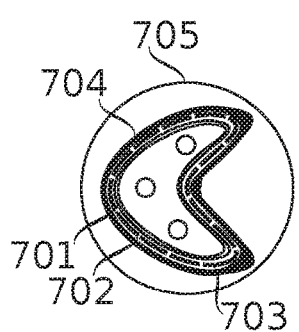

FIGS. 7E-7F show all components engaged (from a side view in FIG. 7E, and in a cross-sectional view in FIG. 7F), with locking tool 705 fully advanced over locking cap 700.

Figure 7G:
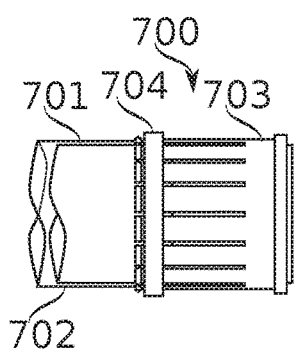
Figure 7H:
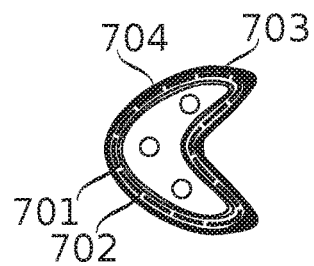

In FIGS. 7G-7H, locking tool 705 has been removed. Sleeve 701 is now locked into place by pressure exerted by closure retainer 704 onto flanges 703, pressing them onto sleeve 701 and against medical instrument 702.

Sleeve Placement Guide Cap

Reference is now made to FIGS. 8A-8F, which schematically illustrate a sleeve-placement guide cap 800, according to some embodiments of the present disclosure. In some embodiments, guide cap 800 assists during insertion of a medical instrument 802 (for example, an endoscope such as a colonoscope, or another medical instrument) to a sleeve 801.

In some embodiments, a sleeve 801 for a medical instrument 802 is configured (e.g., by its shape) so that proper fitting of the sleeve 801 comprises a particular relative rotational orientation of the sleeve 801 and medical instrument 802. For a flexible sleeve 801, this orientation may only one of a plurality of fitting orientations which could happen, even though it is the preferred orientation for fitting. Additionally or alternatively, in some embodiments, the sleeve end is vulnerable to cutting or tearing by medical instrument 802 (e.g., medical instrument 802 comprises a sharp corner or edge) so that it is a potential advantage to hold sleeve 801 away from the medical instrument 802 during insertion, releasing it only after insertion is substantially complete. Additionally or alternatively, in some embodiments, a terminal portion of medical instrument 802 comprises a distal cross-section larger than a more proximal cross-section; and sleeve 801 is sized to conform to the more proximal cross-section—but elastic enough to be stretched to allow the larger cross-section to pass through it. A potential advantage of guide cap 801 in this (and optionally other) situations is to hold the sleeve stretched open to reduce resistance to insertion. In some embodiments, a clip and/or band is configured to collapse and force a distal end of sleeve 801 to assume an intended configuration (e.g., clamping sleeve 801 to medical instrument 802) when released, and this clip is held into a more open configuration by guide cap 800.

In some embodiments, a distal end of sleeve 801 is provided fitted to a guide cap 800, and/or marked so that a guide cap 800 may be reliably seated by an end user. FIG. 8A shows guide cap 800 seated on sleeve 801. Closure retainer 804 is in the locking position, forcing flanges 803A of flange body 803 onto sleeve 801, and from there onto holding body 805. Holding body 805, in some embodiments, comprises a body which occupies a portion of a lumen defined by flanges 803A, but separated from flanges 803A enough to allow an end of sleeve 801 to be inserted between flanges 803A and holding body 805. Accordingly, in the closed-cap position, sleeve 801 is clamped between holding body 805 and flanges 803A.

FIG. 8B illustrates a concave, non-circular cross-section of sleeve 801 clamped to guide cap 800. In some embodiments, another cross-sectional perimeter shape is used, for example a circular perimeter shape, or a non-circular perimeter shape such as a roughly polygonal shape.

In FIG. 8C, the medical instrument has been inserted up to the end of the sleeve, which is held in its proper shape and/or orientation by guide cap 800. Optionally, guide cap also comprises a more distal extension which is shaped to guide medical instrument 802 into position (e.g., by gradually funneling it into the correct orientation, and/or by preventing its advance in an incorrect orientation). FIG. 8D shows a cross-sectional view of the configuration of FIG. 8C.

In FIG. 8E, closure retainer 804 has been moved to the cap-open position, releasing guide cap 800 from the sleeve 801. FIG. 8F separately shows cross sectional views of medical instrument 802 and sleeve 801; and guide cap 800 and the layers of its components.

Clamping Tip

Reference is now made to FIGS. 9A-9D, which illustrate attachment of a flange-clamped adaptor tip 900 to a medical instrument 902, according to some embodiments of the present disclosure.

In some embodiments, medical instrument 902 is supplied with one or more auxiliary functions by a device comprising adaptor tip 900. For example, as shown, adaptor tip 900 comprises a supply and/or evacuation tube 907, attached to adaptor tip 900 via atraumatic bumper 906. Other functions which could be attached include lighting (e.g., LEDs) and/or sensors (e.g., cameras, pressure transducers, and/or electrodes).

Figure 9A:
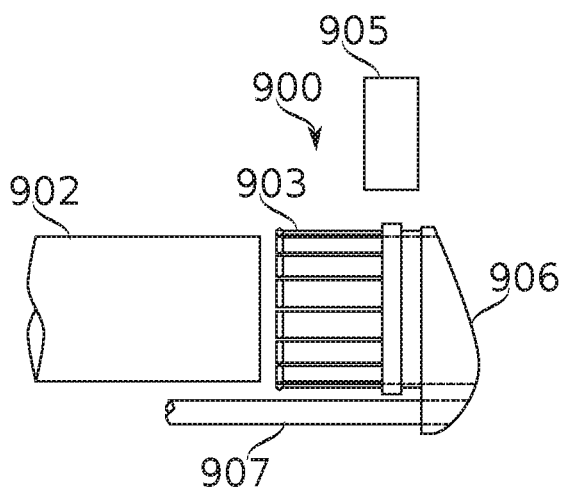
FIGS. 9A-9D illustrate attachment of a flange-clamped adaptor tip to a medical instrument, according to some embodiments of the present disclosure.
Figure 9B:
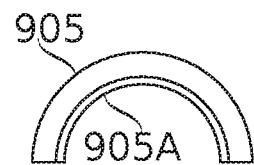

In some embodiments, adaptor tip 900 also comprises flanges 903 and closure retainer 904. Movement of locking body 904 converts adaptor tip 900 between a locked and unlocked position by radial compression of flanges 903. FIG. 9A shows adaptor tip 900 in an unlocked configuration, with medical instrument 902 positioned in preparation for locking.

Figure 9C:
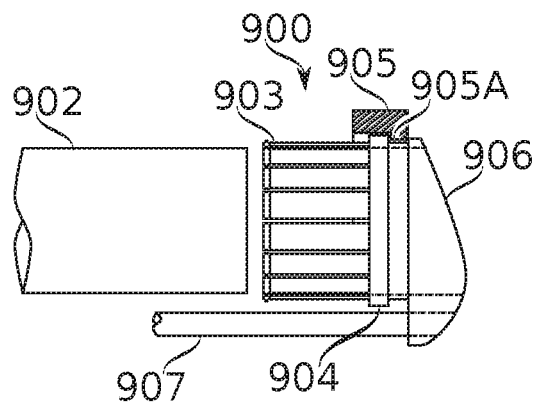

In some embodiments, closure retainer 904 is a low profile retainer (for example, as described in relation to FIGS. 7A-7H). Locking tool 905, in some embodiments (FIG. 9B), is used to move closure retainer 904 between locked/unlocked positions, e.g., by engagement of closure retainer 904 with ledge 905A. FIG. 9C shows locking tool 905 (in cutaway) engaged with closure retainer 904.

Figure 9D:
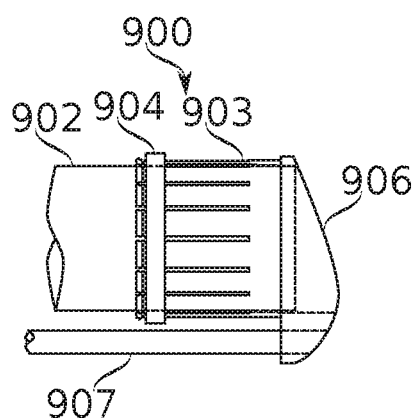

FIG. 9D shows adaptor tip 900 locked to medical instrument 902.

General As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting. In addition, any priority document(s) of this application is/are hereby incorporated herein by reference in its/their entirety.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

What is claimed is:

1. A method of inserting an endoscope to an endoscope sleeve, the method comprising:
    placing a corking body of a sealing cap into an aperture of the endoscope sleeve;
    latching the sealing cap onto the endoscope sleeve to secure the corking body within the aperture, wherein said latching includes collapsing a plurality of tabs of the sealing cap surrounding a circumference of a distal tip of the endoscope sleeve onto the distal tip;
    inflating the endoscope sleeve;
    inserting an endoscope up to a distal portion of the endoscope sleeve;
    unlatching the sealing cap; and
    removing the corking body from the aperture.

2. The method of claim 1, wherein the latching comprises sliding a closure retainer along the sealing cap from an open-cap position to a closed-cap position.

3. The method of claim 1, wherein the tabs surround a non-circular circumference of the distal tip.

4. The method of claim 1, wherein collapsing comprises sliding a closure retainer along the tabs to press the tabs against the distal tip.

5. The method of claim 4, wherein the closure retainer comprises a non-circular inner circumference, and the non-circular inner circumference presses the tabs against the distal tip.

6. The method of claim 4, wherein the collapsing comprises sliding a closure retainer along the tabs, wherein a non-circular inner surface of the closure retainer compresses the tabs radially inward as it slides along the tabs; and wherein the tabs compress against the non-circular circumference of the endoscope sleeve distal tip.

7. The method of claim 6, wherein the non-circular circumferences are each roughly polygonal in a cross section, perpendicular to a longitudinal axis of the endoscope sleeve.

8. The method of claim 1, wherein engaging surfaces on the plurality of tabs comprise protrusions on the tabs which press into the distal tip when the tabs are collapsed onto the distal tip.

9. The method of claim 8, wherein an outer surface of the distal tip is soft, and yields to the engaging surfaces of the protrusions on the tabs.

10. The method of claim 1, wherein engaging surfaces on the plurality of tabs protrude radially inward proximally to the distal tip to secure the corking body within the aperture.

11. The method of claim 1, wherein removing the corking body from the aperture allows the inflated endoscope sleeve to deflate.

12. The method of claim 5, wherein inflating applies distally directed forces which press the tabs more strongly against the distal tip.

13. The method of claim 1, wherein inflating increases a diameter of the endoscope sleeve to a diameter larger than that of the endoscope.

14. The method of claim 1, wherein inserting comprises advancing the distal tip of the endoscope until the distal tip is seated against a stop.

15. A method of inserting a medical instrument to a protective sleeve, the method comprising:
    placing a corking body of a sealing cap into an aperture of the protective sleeve;
    latching the sealing cap onto the protective sleeve to secure the corking body within the aperture, wherein said latching includes collapsing a plurality of tabs of the sealing cap surrounding a circumference of a distal tip of the protective sleeve onto the distal tip;
    inflating the protective sleeve;
    inserting the medical instrument up to a distal portion of the protective sleeve;
    unlatching the sealing cap; and
    removing the corking body from the aperture.

* * * * *

UNITED STATES PATENT AND TRADEMARK OFFICE
CERTIFICATE OF CORRECTION

PATENT NO. : 11,510,554 B1
APPLICATION NO. : 16/924341
DATED : November 29, 2022
INVENTOR(S) : Brad D. Aurilia et al.

It is certified that error appears in the above-identified patent and that said Letters Patent is hereby corrected as shown below:

On the Title Page

Item (73) Assignee, Line 1:
"Motus GI Methical Technologies Ltd."
Should be changed to:
-- Motus GI Medical Technologies Ltd. --

Signed and Sealed this
Second Day of May, 2023

Katherine Kelly Vidal
*Director of the United States Patent and Trademark Office*